US006756043B2

(12) United States Patent
Tsang et al.

(10) Patent No.: US 6,756,043 B2
(45) Date of Patent: Jun. 29, 2004

(54) COMPOSITIONS AND METHODS FOR DETECTING ADULT *TAENIA SOLIUM*

(75) Inventors: Victor C. W. Tsang, Decatur, GA (US); Patricia P. Wilkins, Atlanta, GA (US); James C. Allan, Sandwich (GB)

(73) Assignee: The United States of America as represented by the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 10/072,722

(22) Filed: Feb. 5, 2002

(65) Prior Publication Data

US 2002/0106377 A1 Aug. 8, 2002

Related U.S. Application Data

(62) Division of application No. 09/454,753, filed on Dec. 6, 1999, now Pat. No. 6,379,906.
(60) Provisional application No. 60/111,334, filed on Dec. 7, 1998.

(51) Int. Cl.[7] ........................ A61K 39/00; G01N 33/53; C12N 1/00
(52) U.S. Cl. ............................... 424/265.1; 424/190.1; 424/266.1; 424/269.1; 435/805; 435/810; 435/7.2; 435/7.92; 435/7.22
(58) Field of Search ........................... 426/190.1, 265.1, 426/269.1, 266.1; 435/7.2, 7.22, 7.92, 810, 805, 34; 436/526, 809, 811

(56) References Cited

U.S. PATENT DOCUMENTS 281,061 A * 7/1883 Zuk et al.
5,354,660 A 10/1994 Tsang et al.

OTHER PUBLICATIONS

Allan et al., "Immunodiagnosis of Taeniasis by Coproantigent Detection," *Parasitol.*101:473–477 (1990).
Allan et al., "Coproantigen Detection for Immunodiagnosis of Echinococcosis and Taeniasis in Dogs and Humans," *Parasitol.* 104:347–355 (1992).
Allan et al., "Dipstick Dot ELISA for the Detection of *Taenia* Coproantigens in Humans," *Parasitol.* 107:79–85 (1993).
Brandt et al., "A Monoclonal Antibody–Based ELISA for the Detection of Circulating Excretory–Secretory Antigens in *Taenia saginata* Cysticercosis," *Intl. J. Parasito.* 22:471–477 (1992).
Chapman et al., Isolation and Characterization of Species–Specific DNA Probes from *Taenia solium* and *Taenia saginata* and Their Use in an Egg Detection Assay, *J. Clin. Microbiol.* 33:1283–1288 (1995).
Ko et al., "Evaluation of Excretory/Secretory Products of Larval *Taenia solium* as Diagnostic Antigens for Porcine and Human Cysticercosis," *J. Helminthol.* 72:147–154 (1998).
Maass et al., "Detection of *Taenia solium* Antigens in Merthiolate–Formalin Preserved Stool Samples," *Trop. Med. Parasitol.* 42:112–114 (1991).
McManus, "Improved Diagnosis as an Aid to Better Surveillance of *Taenia solium* Cysticercosis, a Potential Public Health Treat to Papua New Guinea," *Papua New Guinea Med. J.* 38:287–294 (1995).
Varma et al., "Sero–Diagnosis of Infection with Metacestodes of *Taenia solium* in Pigs, and Taeniasis in Man and Dogs by Indirect Haemagglutination Assay," *Indian J. Animal Sci.* 56:621–627 (1986).
Wilkens et al., Annual Meeting of the American Society of Tropical Medicine and Hygiene, Lake Buena Vista, FL (USA), Dec. 7–11, 1997.

* cited by examiner

*Primary Examiner*—Mark Navarro
*Assistant Examiner*—Padma Baskar
(74) *Attorney, Agent, or Firm*—Klarquist Sparkman, LLP

(57) ABSTRACT

Compositions and methods for the detection of adult *Taenia solium* and the diagnosis and treatment of *T. solium* infection are described. The compositions contain one or more adult *T. solium* polypeptides. The polypeptides are useful as diagnostic agents for the detection of adult tapeworm infection. More preferably, the polypeptides are *T. solium* glycoprotein antigens referred to herein as *T. solium* excretory/secretory (TS/ES) polypeptides. The most preferred TS/ES polypeptide has a molecular weight of approximately 33 kDa, 38 kDa, or 42 kDa as determined by SDS-PAGE analysis.

13 Claims, No Drawings

COMPOSITIONS AND METHODS FOR DETECTING ADULT *TAENIA SOLIUM*

This patent application is a divisional application of U.S. patent application Ser. No. 09/454,753 filed Dec. 6, 1999, now U.S. Pat. No. 6,379,906 which claims priority to U.S. Provisional Patent Application No. 60/111,334 filed Dec. 7, 1998.

This invention was made by the Centers for Disease Control, an agency of the United States Government.

FIELD OF THE INVENTION

The present invention relates to the fields of microbiology and immunology and more specifically relates to compositions and methods for diagnosing taeniasis. In particular, the invention pertains to isolated adult *Taenia solium* antigens and their use in immunoassays.

BACKGROUND OF THE INVENTION

*Taenia solium*, also referred to as the pork tapeworm, is a helminth that exists in both a mature tapeworm form and a larval form. The lifecycle of *T. solium* begins when a pig, the intermediate host, ingests tapeworm eggs excreted in the feces of a tapeworm carrier. The larvae hatch from the eggs and invade most tissues of the pig, giving rise to the disease cysticercosis.

When humans ingest raw or undercooked meat from cysticercotic pigs, tapeworm, or taeniasis, develops. Patients with taeniasis exhibit symptoms such as epigastric discomfort, nausea, insomnia, anorexia, irritability, diarrhea and weight loss. Occasionally, individual segments of the tapeworm that are self-contained hermaphroditic reproductive units, referred to as proglottids, may obstruct the appendix, biliary duct, or pancreatic duct, causing severe pain and possible organ damage. These infected individuals become carriers of the tapeworm which produces eggs that are excreted in the feces, thereby continuing the life cycle of the parasite.

Humans may ingest *T. solium* eggs present in contaminated food and water and serve as intermediate hosts. After *T. solium* eggs are ingested, cysticerci may develop in the subcutaneous tissues, muscles, heart, lungs, liver, brain, and eye. Although small numbers of viable cysticerci fail to produce symptoms in the infected host, death of the larvae stimulate a marked inflammatory reaction, fever, muscle pains, and eosinophilia. If the larvae invade the central nervous system, the host may present with meningoencephalitis, epilepsy, and other neurologic or psychiatric manifestations.

The various manifestations of neurologic dysfunction caused by *T. solium* infection are collectively termed neurocysticercosis. Although neurocysticercosis can include many neurological symptoms, epilepsy is the most common symptom. In fact, *T. solium* is considered the leading infectious cause of epileptic seizures worldwide. Additionally, *T. solium*/neurocysticercosis has a current worldwide toll of 50 million cases with 50,000 deaths each year.

Neurocysticercosis is rarely acquired in the United States; however, the disease is common in Latin America, Asia, Russia and Eastern Europe. In Mexico, the mean rate for cysticercotic pigs in inspected slaughterhouses during 1980–1981 was 1.55%, and in rural areas of Mexico and South America where sewage disposal is limited, the number of cysticercotic pigs can be in excess of 5%. In these and other developing countries, the parasite causes a substantial economic burden to the pork industry. Additionally, due to the increased travel and immigration from highly endemic areas, detection and treatment of *T. solium*-related diseases has become a U.S. public health priority.

Because humans are the primary hosts of the tapeworm parasite, the diagnosis and treatment of adult tapeworm carriers is crucial for interrupting transmission of taeniasis and cysticercosis. Furthermore, distinction between the adult and larval forms of *T. solium* is important since both infections are asymnptomatic initially, but result in two different diseases, taeniasis and cysticercosis, respectively, which require two different routes of treatment.

Classically, taeniasis has been detected by direct parasitologic examination of stool samples. Detection methods, based on microscopic observation of eggs or proglottids in feces, are neither sensitive nor specific. Direct examination of Taenia eggs is equivocal and requires examination of expelled proglottids for speciation. Recently, coproantigen detection assays have been developed. However, these assays are not specific for *T. solium*. For example, they are unable to distinguish between *T. solium* and *T. saginata* infections. A more recent method involving DNA probes specific for *T. solium* or *T. saginata* has been developed that uses species-specific primers to differentiate these two tapeworm infections. This technique relies on the amplification of parasite DNA obtained from parasite eggs or proglottids present in the stool sample. Although the polymerase chain reaction can detect the presence of a single egg, the intermittent passage of eggs in the stool limits the usefulness of this assay.

An early and specific diagnosis of taeniasis may prevent cysticercosis and allow treatment for taeniasis before painful symptoms arise. Therefore, there is a need for sensitive, specific, and inexpensive assays that can detect the presence of the *T. solium* adult worm.

SUMMARY OF THE INVENTION

Compositions and methods for detecting and diagnosing *Taenia solium* are provided herein. The compositions contain one or more of the *T. solium* polypeptides described below. The polypeptides are useful in immunoassays for the detection of *T. solium* in biological samples. The preferred polypeptides are specific to the adult form of *T. solium*. The polypeptides are useful as diagnostic agents for the detection of adult tapeworm infection. More preferably, the polypeptides are *T. solium* glycoprotein antigens referred to herein as *T. solium* excretory/secretory (TS/ES) polypeptides. The most preferred TS/ES polypeptide is one having a molecular weight of approximately 33 kDa, 38 kDa, or 42 kDa as determined by SDS-PAGE analysis. The compositions also include combinations of these preferred polypeptides or *T. solium* peptides, which are fragments of the TS/ES polypeptide. Preferred polypeptides and fragments thereof are immunoreactive with *T. solium* antibodies. The preferred polypeptides and fragments thereof are specific for *T. solium* and are not cross-reactive with antibodies present in *T. saginata* serum samples.

The preferred methods provided in herein are immunoassays directed toward the detection of *T. solium* antibodies in biological samples such as biological fluids. The assays detect antibodies to the adult *T. solium* organism and are thereby capable of distinguishing between infection by the adult tapeworm and larval forms of *T. solium*. The preferred immunoassay utilizes one or more of the isolated TS/ES adult antigens or immunoreactive portions thereof, as described herein, for the detection of anti-TS/ES antibodies in the biological sample. The polypeptides, or antigens, are preferably labeled, either directly or indirectly with a detectable label, such as a radioisotope or a detectable molecule or protein.

Diagnostic and analytical methods and kits may be developed for detection and measurement of *T. solium* antibodies in a variety of biological samples. The method and kit can be in any configuration well known to those of ordinary skill in the art.

Accordingly, it is an object of the present invention to provide means for detecting *T. solium* carriers and thus prevent the spread of *T. solium* from one host to another.

It is another object of the present invention to provide a method for the detection of *T. solium*, particularly *T. solium* infection in humans, that is sensitive and accurate.

It is another object of the present invention to provide a sensitive method for the diagnosis of taeniasis.

It is another object of the present invention to provide a diagnostic method capable of distinguishing adult *T. solium* infection from larval *T. solium* infection (cysticercosis).

It is another object of the present invention to provide a diagnostic method capable of distinguishing adult *T. solium* infection from other helminthic infections, particularly *T. saginata* infections.

It is yet another object of the present invention to provide a rapid, simple, and inexpensive immunoassay for the detection of antibodies to adult *T. solium* in an easily obtained biological fluid such as blood serum, plasma or saliva.

One advantage of the invention described herein is that the methods are rapid and simple to conduct, and the results can be interpreted without the use of instrumentation or special temperature conditions, which is optimal for use in poor, underdeveloped countries where *T. solium* is often endemic.

These and other objects, features and advantages of the present invention will become apparent after a review of the following detailed description of the disclosed embodiments and the appended claims.

DETAILED DESCRIPTION

Compositions and methods for detecting *T. solium* infection and diagnosing and monitoring diseases related to *T. solium* infection are provided. The compositions contain one or more isolated, immunogenic polypeptides, or immunogenic fragments thereof, derived from the *T. solium* adult helminth. The preferred polypeptides are *T. solium* secretory/excretory (TS/ES) polypeptides derived from glycoprotein antigens.

The *T. solium* polypeptides are useful in vitro as research tools for studying *T. solium* in general and *T. solium* related diseases such as taeniasis. The *T. solium* polypeptides are also useful as diagnostic reagents in immunoassays as described in more detail below. The *T. solium* polypeptides are preferably immobilized or labeled with a detectable label and incubated with a biological sample to allow binding of the polypeptide to adult *T. solium* antibodies in the biological sample. Detection of the antibody-antigen (or antibody-polypeptide) complex indicates the presence of a *T. solium* infection.

The methods described herein include assays for the detection or quantitation of anti-*T. solium* antibodies in a biological sample, such as a biological fluid. The *T. solium* polypeptides, or fragments thereof, provided herein are used as reagents in the assays.

Definitions

The terms "a", "an" and "the" as used herein are defined to mean "one or more" and include the plural unless the context is inappropriate.

The terms "polypeptide", "peptide" and "protein", as used herein, are interchangeable and are defined to mean a biomolecule composed of two or more amino acids linked by a peptide bond.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

*Taenia solium* Polypeptides

The compositions provided herein are isolated *T. solium* polypeptides. The polypeptides are isolated from adult *T. solium* organism preparations. Preferably, the polypeptides are secretory/excretory (TS/ES) polypeptides produced by viable adult *T. solium* organisms or isolated from *T. solium* cell culture.

A more preferred polypeptide is an adult *T. solium* TS/ES polypeptide having a molecular weight of approximately 33 kDa, 38 kDa, or 42 kDa as determined by sodium dodecyl sulfate-polyacrylamide gel electrophoresis (SDS-PAGE) analysis. Compositions containing combinations of these polypeptides, or immunogenic fragments thereof, are particularly useful in diagnostic assays as described in more detail below. Most preferably, the polypeptide is an adult *T. solium* TS/ES polypeptide having a molecular weight of approximately 32.7 kDa, 37.8 kDa, or 42.1 kDa, as determined by SDS-PAGE analysis. As mentioned above, the preferred polypeptides also include fragments of the polypeptides described herein having the same antigenicity or the functional equivalent thereof.

The polypeptides are specific to the adult *T. solium* and exhibit minimal or no cross-reactivity with antisera from patients infected with the larval *T. solium* organism or other cestodes, such as *T. saginata*. The polypeptides bind with high specificity and avidity to antibodies in biological fluid samples, such as blood sera, blood plasma or saliva, taken from individuals infected with adult *T. solium*.

The *T. solium* polypeptides described herein have a variety of uses. For example, the *T. solium* polypeptides may be employed as research tools to develop affinity columns for isolating *T. solium* antibodies. Also, the polypeptides may be labeled with a label or reporter group and employed for visualization and quantitation in the assays described below using detection techniques such as autoradiographic and membrane binding techniques. The reporter group or label is commonly a fluorescent or radioactive group or an enzyme. Such applications provide important diagnostic and research tools. In addition, the polypeptides may be useful as immunogenic agents, and may, therefore, be administered to a human as a vaccine or to animals for the generation of anti-*T. solium* antibodies.

Labeled Reagents

When labeled with a detectable biomolecule or chemical, the *T. solium* polypeptides described above are useful for purposes such as in vivo and in vitro diagnostics and laboratory research using the methods and assays described below. Various types of labels and methods of conjugating the labels directly or indirectly to the polypeptides and antibodies are well known to those skilled in the art and include enzymes, radioisotopes, and fluorescent, luminescent and chromogenic substances including colored particles such as colloidal gold and latex beads. Suitable immunoassays include enzyme-linked immunosorbent assays (ELISA) and radioimmunoassays. Several specific labels are set forth below.

For example, the polypeptides and antibodies are conjugated to a radiolabel such as, but not restricted to, $^{32}$P, $^{3}$H, $^{14}$C, $^{35}$S, $^{125}$I, or $^{131}$I. Detection of a label can be by methods such as scintillation counting, gamma ray spectrometry or autoradiography.

Bioluminescent labels, such as derivatives of firefly luciferin, are also useful. The bioluminescent substance is covalently bound to the polypeptide by conventional methods, and the labeled polypeptide is detected when an enzyme, such as luciferase, catalyzes a reaction with ATP causing the bioluminescent molecule to emit photons of light.

Fluorogens may also be used as labels. Examples of fluorogens include fluorescein and derivatives, phycoerythrin, allo-phycocyanin, phycocyanin, rhodamine, and Texas Red. The fluorogens are generally detected by a fluorescence detector.

The polypeptides and antibodies can alternatively be labeled with a chromogen to provide an enzyme or affinity label. For example, the polypeptide can be biotinylated so that it can be utilized in a biotin-avidin reaction, which may also be coupled to a label such as an enzyme or fluorogen. Alternatively, the polypeptide can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, peptides may be labeled with colloidal gold for use in immunoelectron microscopy in accordance with methods well known to those skilled in the art.

The location of an infection by the *T. solium* tapeworm can be determined by labeling an antibody as described above and detecting the label in accordance with methods well known to those skilled in the art, such as immunofluorescence microscopy using procedures such as those described by Warren and Nelson, *Mol. Cell. Biol.* 7: 1326–1337 (1987). For example, the *T. solium* antibodies can be labeled with short lived isotopes to enable visualization of *T. solium* antigens in vivo using positron emission tomography or other modern radiographic techniques to locate infectious sites.

Alternatively, the polypeptide may be labeled indirectly by reaction with labeled substances that have an affinity for immunoglobulin, such as protein A or G or second antibodies. When using secondary antibodies a suitable immunoassay is an immunoblot or Western blot. Additionally, the polypeptide may be conjugated with a second substance and detected with a labeled third substance having an affinity for the second substance conjugated to the polypeptide. For example, the polypeptide may be conjugated to biotin and the antibody-biotin conjugate detected using labeled avidin or streptavidin. Similarly, the polypeptide may be conjugated to a hapten and the conjugate detected using labeled anti-hapten antibody. These and other methods of labeling polypeptides and assay conjugates are well known to those skilled in the art.

Detection of *T. solium* Antibodies

The methods provided herein include diagnostic assays to detect and quantify adult *T. solium* antibodies. The methods permit detection of circulating *T. solium* antibodies in order to indicate the presence or level of *T. solium* tapeworm infection. Importantly, because the polypeptides described herein contain antigens that are specific to the adult tapeworm, while other known methods are specific for larval forms of *T. solium*, the diagnostic method allows an infection by the adult *T. solium* tapeworm to be distinguished from an infection by the *T. solium* larval form. Distinction between these two forms of *T. solium* is important because both infections are asymptomatic initially, but result in two different diseases, taeniasis and cysticercosis, which require two different methods of treatment. While taeniasis, or tapeworms, may be treated by drug therapy, treatment of cysticercosis and the potential associated neurologic dysfunction is more problematic. Therefore, the methods described herein provide a means for early and specific diagnosis, monitoring, and treatment of taeniasis that may prevent infection by eggs resulting in cysticercosis.

An immunoassay is performed for the detection of *T. solium* antibody in a sample as follows: A biological sample, such as a body fluid, is collected or obtained using methods well known to those skilled in the art. The sample containing the adult *T. solium* tapeworm antibodies to be detected is preferably obtained from a biological fluid, such as, but not limited to, blood serum, blood plasma, saliva, urine, spinal fluid, fermentation fluid, lymph fluid, and tissue culture fluid. The sample may be diluted, purified, concentrated, filtered, dissolved, suspended or otherwise manipulated prior to immunoassay to optimize. the immunoassay results.

To detect *T. solium* tapeworm antibodies, the sample is incubated with one or more of the *T. solium* polypeptides described above. The polypeptide may be labeled or conjugated to a solid phase bead or particle as also described herein. The labeled polypeptide binds to an anti-*T. solium* antibody present in the biological sample to form an antibody-antigen complex, and the complex is detected using methods well known to those skilled in the art. Such methods include immunological techniques such as enzyme linked immunosorbant assays, radioimmunoassays, chemiluminescent assays, or other types of assays involving antibody-antigen complexes known to those skilled in the art.

Current binding assay technology benefits from the diversity of detection systems developed that use enzyme-catalyzed chromogenic reactions, radionuclides, chemiluminescence, bioluminescence, fluorescence, fluorescence polarization and a variety of potentiometric and optical biosensor techniques.

Binding assays rely on the binding of analyte by analyte receptors to determine the concentrations of analyte in a sample. Analyte-receptor assays can be described as either competitive or non-competitive. Non-competitive assays generally utilize analyte receptors in substantial excess over the concentration of analyte to be determined in the assay. Sandwich assays are examples of non-competitive assays, that comprise one analyte receptor frequently bound to a solid phase and a second analyte receptor labeled to permit detection. The analyte first binds to the analyte receptor bound to a solid phase and the second labeled analyte receptor is then added to facilitate quantitation of the analyte. Bound analyte can easily be separated from unbound reagents, such as unbound labeled first analyte receptors, due to the use of an analyte receptor bound to a solid phase.

Competitive assays generally involve a sample suspected of containing analyte, an analyte-analogue conjugate, and the competition of these species for a limited number of binding sites provided by the analyte receptor. Competitive assays can be further described as being either homogeneous or heterogeneous. In homogeneous assays all of the reactants participating in the competition are mixed together and the quantity of analyte is determined by its effect on the extent of binding between analyte receptor and analyte-conjugate or analyte analogue-conjugate. The signal observed is modulated by the extent of this binding and can be related to the amount of analyte in the sample. The binding of the antibody to the analyte analogue-enzyme conjugate decreases the activity of the enzyme relative to the activity observed when the enzyme is in the unbound state. Due to competition between unbound analyte and analyte analogue-enzyme conjugate for analyte-receptor binding sites, as the analyte concentration increases the amount of unbound analyte analogue-enzyme conjugate increases and thereby increases the observed signal. The product of the enzyme reaction may then be measured kinetically using a spectrophotometer.

Heterogeneous, competitive assays require a separation of analyte analogue conjugate bound to analyte receptor from the free analyte analogue conjugate and measurements of either the bound or the free fractions. Separation of the bound from the free may be accomplished by removal of the analyte receptor and anything bound to it from the free analyte analogue conjugate by immobilization of the analyte receptor on a solid phase or precipitation. The amount of the analyte analogue conjugate in the bound or the free fraction can then be determined and related to the concentration of the analyte in the sample. Normally the bound fraction is in a convenient form, for example, on a solid phase, so that it can be washed, if necessary, to remove remaining unbound analyte analogue conjugate and the measurement of the bound analyte analogue conjugate or related products is. facilitated. The free fraction is normally in a liquid form that is generally inconvenient for measurements. If multiple analytes are being determined in a single assay, the determination of the free fraction of analyte analogue conjugate for each analyte is made impossible if all are mixed in a single liquid unless the responses of the individual analyte analogue conjugates can be distinguished in some manner. However, detecting the free fraction of analyte analogue conjugate in assays that are visually interpreted is a distinct advantage because the density of the color developed in such assays is generally proportional to the analyte concentration over much of the range of analyte concentration.

The preferred diagnostic method is an immunoblot assay, such as the enzyme-linked immunotransfer blot assay described by Tsang et al., *J. Infect. Dis.* 159:50–9 (1989) or *Methods Enzymol* 92:377–91 (1985). The immunoblot assay is conducted by contacting the biological sample, such as blood serum from the patient to be diagnosed with *T. solium* infection, with one or more of the *T. solium* polypeptides described herein, and detecting the binding of antibody in the sample to the polypeptide reagent.

Preferably, the reagent used in the immunoblot assay is one or more of the *T. solium* TS/ES glycoprotein antigens having molecular weights of approximately 32 kDa, 38 kDa and 42 kD, most preferably 32.7 kDa, 37.8 kDa and 42.1 kDa, derived from the adult *T. solium* tapeworm. In preliminary studies, an immunoblot assay utilizing all three TS/ES polypeptides, showed 95% (69/73) reactivity when tested with serum from individuals with parasitologically confirmed *T. solium* tapeworm infections. Additionally, out of 193 serum samples from patients with other parasitic diseases, none of the samples contained antibodies that reacted with said TS/ES polypeptide antigens. (See Table 1, below.) The calculated predictive positive value of the immunoassay was 100% (69/69), and the predictive negative value was 98% (193/197). These results indicate that an immunoblot assay using all three of the above described TS/ES polypeptides has high specificity for the diagnosis of taeniasis, or *T. solium* tapeworm infection.

It is to be understood that the assay methods are contemplated to include the use of the isolated *T. solium* polypeptides as described above and fragments or derivatives of the *T. solium* polypeptides described herein as long as the polypeptide fragments or derivatives retain antigenic activity or display an equivalent antigenic activity of the entire immunogenic polypeptides. These fragments or derivatives include peptides with antigenic activity that have amino acid substitutions or have other molecules attached to amino acid functional groups.

Kit for Detecting the Presence of *T. solium*

A kit for detecting the presence and quantity of adult *T. solium* peptides is provided. The kit can be in any configuration well known to those of ordinary skill in the art and is useful for performing one or more of the methods described herein for the detection of *T. solium* in biological samples or for the detection or monitoring of *T. solium* infection in a patient or carrier. The kits are convenient in that they supply many if not all of the essential reagents for conducting an assay for the detection of T. solium in an environmental or biological sample.

The reagents may be premeasured and contained in a stable form in vessels or on a solid phase in or on which the assay may be performed, thereby minimizing the number of manipulations carried out by the individual conducting the assay. In addition, the assay may be performed simultaneously with a standard that is included with the kit, such as a predetermined amount of polypeptide, so that the results of the test can be validated or measured.

The kit preferably contains one or more *T. solium* polypeptides that can be used for the detection of *T. solium* antibodies in a sample. The kit can additionally contain the appropriate reagents for binding or hybridizing the polypeptides to their respective *T. solium* antibodies in the sample as described herein and reagents that aid in detecting the bound polypeptides. The kit may additionally contain equipment for safely obtaining the sample, a vessel for containing the reagents, the appropriate paper, membrane or filter for separating complexes from non-reacted reagents, a timing means, a buffer for diluting the sample, and a colorimeter, reflectometer, or standard against which a color change may be measured.

In a preferred embodiment, the reagents, including the polypeptide, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

The assay kit includes but is not limited to reagents to be employed in the following techniques; competitive and non-competitive assays, radioimmunoassay, bioluminescence and chemiluminescence assays, fluorometric assays, sandwich assays, immunoradiometric assays, dot blots, enzyme linked assays including immunoblots and ELISAs, and immunocytochemistry. Materials used in conjunction with these techniques include, but are not limited to, microtiter plates, antibody coated strips or dipsticks for rapid monitoring of urine or blood. For each kit, the range, sensitivity, precision, reliability, specificity and reproducibility of the assay are established. Intraassay and interassay variation is established at 20%, 50% and 80% points on the standard curves of displacement or activity.

More preferably, the assay kit utilizes ELISA or blot techniques and provides instructions, *T. solium* polypeptides, and anti-immunoglobulin antibodies conjugated to a detectable molecule. The kit is useful for the detection or measurement of *T. solium* in biological fluids of humans with and without taeniasis.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims:

EXAMPLE 1

Identification of Immunoreactive Adult *T. solium* Antigens

Immunoreactive adult *T. solium* antigens were identified as follows:

Materials and Methods

Parasite Materials

*Taenia solium* tapeworms were harvested from immunosuppressed hamsters in accordance with the procedures of Allan et al., *Ann. Trop. Med. Parasitology* 85:573–6 (1991). Briefly, adult worms, 20 to 25 centimeters in length, were harvested from immunosuppressed hamsters approximately six to eight weeks after infection with porcine *T. solium* cysts. Tapeworms were washed in antibiotics (penicillin and streptomycin) and placed into 25 $cm^2$ tissue culture flasks in minimal essential media (MEM, GIBCO, Grand Island, N.Y.) supplemented with penicillin/streptomycin and fungizone. Culture supernatants containing TS/ES proteins were collected following in vitro culture of *T. solium* tapeworms. For most experiments, TS/ES proteins were collected after the first 24 hours of culture. This material was concentrated approximately ten-fold using a PM-10™ membrane (Amicon, Beverly, Mass.) and stored frozen. After thawing, protease inhibitors were added.

The ES preparations used in some early experiments represented pooled supernatants collected from days 5 to 16 of culture. The media was changed every eight hours for the first 24 hours, then every 24 hours for the next two days. After the first 72 hours, the culture media was removed and replaced at five-day intervals. The culture supernatants from days 5 to 16 were pooled, concentrated with polyethylene glycol (molecular weight 6000), and lyophilized. The resultant material containing TS/ES antigens was frozen at --70° C., then reconstituted with 5.0 ml distilled water containing final concentrations of the following protease inhibitors: leupeptin (1.0 μg/ml, Calbiochem, La Jolla, Calif.), pepstatin (1.0 μg/ml, Calbiochem, La Jolla, Calif.), and Pefabloc™ protease inhibitor (1 mM, Boehringer Mannheim, Indianapolis, Ind.). Other preparations of TS/ES proteins were evaluated that represented supernatants collected after differing periods of culture, ranging from 3 to 15 days.

*T. solium* cyst extracts were prepared in accordance with the method of Tsang et al., *J. Infect. Dis.* 159:50–9 (1989). Lentil lectin unbound and bound fractions were used in immunoblot experiments and loaded onto gels at 0.2 and 0.05 μg/mm, respectively.

SDS-PAGE and Immunoblot

Sodium dodecyl sulfate-polyacrylamide gel electrophoresis (SDS-PAGE) and immunoblot procedures were performed as described in Tsang et al., *J. Infect. Dis.* 159:50–9 (1989). Briefly, TS/ES antigens were treated for electrophoresis with 1% SDS, 0.1% bromophenol blue in 0.01 M Tris-HCl, pH 8.0 at 65° C. for 15–20 minutes and loaded at 4 μl/mm. For analysis of individual serum samples, blots were cut into identical three-mm strips. Cut strips were stored in. the presence of 0.1% $NaN_3$ at −70° C. until used. Sera were diluted 1:100 in PBS/5% non-fat dry milk/0.3% Tween and incubated with the blotted antigens for one hour at room temperature. In isotype experiments, TS/ES specific isotypes were detected using mouse monoclonal antibodies directed against the individual human isotypes, as described in Boyer et al., *J. Immunol.* 146:3993–4000 (1991). All reagents for SDS-PAGE and immunoblotting were reagent grade or better, and, unless otherwise noted, were obtained from Mallinchrodt (St. Louis, Mo.). Tris was obtained from Schwartz-Mann (Orangeburg, N.J.).

Serum Samples

Serum samples taken from only persons known to be infected with *T. solium* tapeworms were used to develop and evaluate the sensitivity of the test. Serum samples were collected from individuals infected with *T. solium* tapeworms in Guatemala (n=44), Peru (n=26), and Indonesia (n=3). In some experiments, a taeniasis-positive pool was used, made from five serum samples from persons with confirmed *T. solium* taeniasis. A cysticercosis positive pool was prepared from six persons with computed tomography-confirmed cysticercosis. Individual sera from persons with cysticercosis were collected in Bolivia (n=23).

In immunoblot experiments examining the stage specificity of the TS/ES antigens, a serum sample was used that was obtained from a patient who was confirmed to have taeniasis, but was serologically negative for cysticercosis using the cysticercosis immunoblot. This particular serum sample was used because antibodies in this sample reacted only with the target diagnostic TS/ES antigens in the ES preparation.

All individual disease-specific serum samples were selected on the basis of parasitologic confirmation of infection. All efforts were made to include individual serum samples associated only with one disease. Particularly, in selecting heterologous infection serum samples, an attempt was made to include only samples from *T. solium*-free geographic regions; however, this was not possible in all cases. The *T. saginata* infection sera were collected from individuals in Poland (n=6) and in Peru (n=3). In Peru, parasitologic diagnosis of *T. saginata* infection was confirmed by direct examination of proglottids. Of the 69 echinococcosis sera used, 59 were from individuals infected with *E. granulosus* and ten from individuals infected with *E. muitilocularis.* A pool of normal human sera was prepared from 50 healthy U.S. residents who had no travel history to Taenia-endemic areas.

Results

Identification of Diagnostic Antigens

The validity of using TS/ES antigens in a serologic assay to detect taeniasis cases was investigated. To identify antigens that are specific for taeniasis and not cysticercosis, ES antigens were first separated by SDS-PAGE and evaluated by immunoblot using pools of serum prepared from persons infected with taeniasis or cysticercosis. Antigens that reacted with taeniasis antibodies, but not cysticercosis antibodies, were identified as potential diagnostic targets. A group of two antigens with molecular weights of 32.7 kDa and 37.8 kDa were identified as potential diagnostic targets and appeared to be specific for taeniasis.

TS/ES was examined initially because of the reduced antigenic complexity present in these samples compared with that of extracts prepared from intact tapeworms. The TS/ES collected following the first 24 hours of culture was the least complex preparation examined. Evaluation of culture supernatants collected following several days (3–16) of culture showed that these preparations were much more complex. The 32.7 kDa and 37.8 kDa antigens were present in all preparations of TS/ES that were examined, suggesting that these antigens are synthesized continuously by the tapeworm. An additional antigen of molecular weight 42.1 kDa was present in one TS/ES preparation, collected from days 5 to 16 of culture.

Individual serum samples from taeniasis and cysticercosis patients were evaluated for reactivity with the TS/ES diagnostic antigens (Table 1). Ninety five % (69 of 73) of samples tested from parasitologically confirmed *T. solium* tapeworm infections contained antibodies to the TS/ES antigens. Typically, if a sample was determined to be positive, both the 32.7 kDa and the 37.8 kDa antigens were recognized. In TS/ES preparations that also contained the larger 42.1 kDa antigen, all three antigens were recognized by antibodies present in positive samples, suggesting that these three antigens may be related to each other. Conversely, evaluation using serum samples from patients with cysticercosis showed that very few of these samples contain antibodies that reacted with the target ES antigens. One of 23 samples tested in these experiments contained antibodies that reacted with the TS/ES antigens. Some cysticercosis patients may also be tapeworm carriers; therefore, it was not unexpected to detect antibodies to *T. solium* ES antigens in some samples. Thus, the 32.7 kDa, 37.8 kDa and 42.1 kDa antigens were identified as diagnostic targets.

TABLE 1

Specificity of the *T. solium* ES diagnostic proteins for detecting only *T. solium* taeniasis.

| Infection* | # samples tested | # samples positive |
|---|---|---|
| *T. solium* infections: | | |
| Taeniasis | 73 | 69 |
| Cysticercosis | 23 | 1 |
| Other cestode infections: | | |
| *T. saginata* taeniasis | 8 | 0 |
| Echinococcosis | 69 | 0 |
| *Hymenolepis nana* | 7 | 0 |
| Non-cestode infections: | | |
| Schistosomiasis | 37 | 0 |
| Filariasis | 30 | 0 |
| Ascariasis | 30 | 0 |
| Trichinellosis | 4 | 0 |
| Drancunculiasis | 4 | 0 |
| Protozoal Infections: | | |
| Amebiasis | 4 | 0 |

*Filariasis sera* were collected from individuals infected with onchocerciasis (n = 26) and lymphatic filariasis (n = 4, caused by *Wuchereria bancrofti*). Schistosomiasis infection sera were collected from persons with *S. mansoni, S. haematobium*, and *S. japonicum* infections.

EXAMPLE 2

TS/ES Assay Sensitivity Analysis

The sensitivity of the TS/ES assay was evaluated as follows.

Specificity of TS/ES Immunoblot Assay Between Species

The specificity of the TS/ES immunoblot assay was investigated first with regard to differentiation of *T. solium* and *T. saginata* infections. To determine if *T. saginata* tapeworm carriers generate antibodies to TS/ES antigens, particularly the target diagnostic antigens, serum samples from confirmed *T. saginata* tapeworm carriers were examined for reactivity with the TS/ES antigen using the immunoblot assay described in Example 1, above. For these experiments, serum samples from *T. saginata* tapeworm-infected persons were collected in areas where *T. solium* is not present (Poland, n=6) and in areas where *T. solium* is endemic (Peru, n=3). As shown in Table 1, there were no cross-reacting antibodies present in any *T. saginata* samples that recognized any TS/ES antigens, including the TS/ES diagnostic antigens.

Serum samples from patients with other parasitic diseases were also examined for antibodies to the TS/ES antigens as shown in Table 1. None of the 193 samples examined contained antibodies that reacted with the target TS/ES antigens. The serum battery included 69 serum samples from patients, with echinococcosis, and seven serum samples from patients infected with *Hymenolepis nana*. Some serum samples from echinococcosis patients contained antibodies that reacted with other higher molecular weight antigens in the TS/ES mixture, but not with the diagnostic antigens.

Results from all of the serum samples examined are shown in Table 1. These data were used to calculate a measure of assay performance: the positive predictive and negative predictive values. Using previously published methods to determine assay performance (Galen R S and Gambino S R. Predictive Value and Efficiency of Medical Diagnoses. J Wiley and Sons, p. 30 (1975).), the calculated predictive positive value of the assay was 100% (69/69), and the predictive negative value was 98% (193/197). The cysticercosis-positive samples from Bolivia were excluded from these calculations since they can not be classified as either true positives or true negatives.

Specificity of TS/ES Immunoblot Assay Between Maturation Stages

Completion of the *T. solium* life cycle requires maturation of two different parasite stages through two different hosts. Therefore, an experiment was designed to determine if the diagnostic adult-stage ES antigens were also expressed during the cyst stage. The lentil lectin unbound and bound fractions from cyst extracts were examined for the presence of the analogous TS/ES antigens using a taeniasis-specific serum sample. The taeniasis-specific antibodies did not react with analogous cyst proteins in either the lectin unbound or bound cyst fractions. These results indicate that the diagnostic TS/ES antigens are expressed only by *T. solium* tapeworms and not during the larval stage of the parasite. If the diagnostic TS/ES antigens are present in cyst extracts, they are present either in very low quantities, or have different mobilities in SDS-PAGE.

Isotypes of Anti-TS/ES Antibodies

Specific TS/ES isotypes were assessed for eight taeniasis cases: four samples collected in Peru and four in Guatemala. All serum samples examined contained IgG1 antibodies to the diagnostic TS/ES antigens. In addition, most (7 of 8) serum samples contained IgA antibodies to these antigens. In some older, frequently thawed samples, reactivity of the IgA antibodies was weak, but present. Specific IgM antibodies were present in one of eight samples tested. Anti-TS/ES IgE was not detected in any samples.

The disclosures of all publications cited in this application are hereby incorporated by reference in their entireties in order to more fully describe the state of the art to which this invention pertains.

Modifications and variations of the present compositions and methods will be obvious to those skilled in the art from the foregoing detailed description. Such modifications and variations are intended to come within the scope of the appended claims.

We claim:

1. A composition comprising an isolated, adult *Taenia solium* excretory/secretory polypeptide, wherein the polypeptide has a molecular weight of approximately 33 kDa, 38 kDa, or 42 kDa, determined by SDS-PAGE analysis.

2. The composition of claim 1 wherein the polypeptide has a molecular weight of approximately 32.7 kDa, 37.8 kDa, or 42.1 kDa, as determined by SDS-PAGE analysis.

3. The composition of claim 1 wherein the polypeptide is a mixture of two or more isolated, adult *Taenia solium* excretory/secretory polypeptides having molecular weights of approximately 33 kDa, 38 kDa, or 42 kDa, as determined by SDS-PAGE analysis.

4. The composition of claim 1 wherein the polypeptide is a mixture of two or more isolated, adult *Taenia solium* excretory/secretory polypeptides having molecular weights of approximately 32.7 kDa, 37.8 kDa, or 42.1 kDa, as determined by SDS-PAGE analysis.

5. The composition of claim 1 wherein the polypeptide is a mixture of three isolated, adult *Taenia solium* excretory/secretory polypeptides having molecular weights of approximately 33 kDa, 38 kDa, and 42 kDa, as determined by SDS-PAGE analysis.

6. The composition of claim 1 wherein the polypeptide is a mixture of three isolated, adult *Taenia solium* excretory/secretory polypeptides having molecular weights of approximately 32.7 kDa, 37.8 kDa, and 42.1 kDa, as determined by SDS-PAGE analysis.

7. The composition of claim 1, wherein the polypeptide is immobilized.

8. The composition of claim 7, wherein the polypeptide is immobilized to a solid phase bead or particle.

9. The composition of claim 1, wherein the polypeptide is labeled.

10. The composition of claim 9, wherein the label is a fluorescent molecule, a luminescent molecule, a radiolabel, a chromogenic substance, or an enzyme.

11. A kit comprising the composition of claim 1, wherein the composition is in a vessel or on a solid phase.

12. A kit comprising the composition of claim 1 and instructions for using the kit.

13. A kit comprising the composition of claim 1, wherein the composition in lyophilized.

* * * * *